US006793846B2

(12) United States Patent
Yoshikawa et al.

(10) Patent No.: US 6,793,846 B2
(45) Date of Patent: Sep. 21, 2004

(54) MICROBICIDE COMPOSITIONS

(75) Inventors: Kiyoaki Yoshikawa, Wakayama (JP);
Yoshihiro Yamazaki, Wakayama (JP);
Tetsuya Okano, Wakayama (JP);
Shigeru Tamura, Wakayama (JP);
Noboru Matsuo, Wakayama (JP);
Sumitoshi Ito, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/149,147

(22) PCT Filed: Dec. 8, 2000

(86) PCT No.: PCT/JP00/08716

§ 371 (c)(1),
(2), (4) Date: Aug. 12, 2002

(87) PCT Pub. No.: WO01/41571

PCT Pub. Date: Jun. 14, 2001

(65) Prior Publication Data

US 2003/0155549 A1 Aug. 21, 2003

(30) Foreign Application Priority Data

| Dec. 10, 1999 | (JP) | ............................................. | 11-352217 |
| Feb. 18, 2000 | (JP) | ........................................ | 2000-041092 |
| Mar. 10, 2000 | (JP) | ........................................ | 2000-066815 |
| Apr. 28, 2000 | (JP) | ........................................ | 2000-130276 |

(51) Int. Cl.$^7$ .......................... C01B 11/04; C01B 11/06; C11D 3/395; C11D 7/54; A01N 59/08
(52) U.S. Cl. ........................... 252/187.25; 252/187.24; 252/187.26; 252/187.32; 510/302; 510/303; 510/367; 424/661; 422/37
(58) Field of Search .................... 252/187.28, 187.32, 252/187.24, 187.25, 187.26, 187.27; 510/303, 367, 302; 424/661; 422/37

(56) References Cited

U.S. PATENT DOCUMENTS

| 4,051,034 A | * | 9/1977 | Amon et al. ................. 210/206 |
| 4,229,313 A | * | 10/1980 | Joy .............................. 510/373 |
| 4,271,030 A | | 6/1981 | Brierley et al. |
| 4,418,055 A | | 11/1983 | Andersen et al. |
| 4,474,677 A | * | 10/1984 | Foxlee ................... 252/187.25 |
| 4,731,223 A | * | 3/1988 | Forestier et al. .............. 422/37 |
| 4,783,283 A | * | 11/1988 | Stoddart ...................... 510/373 |
| 5,093,140 A | | 3/1992 | Watanabe |
| 5,120,452 A | * | 6/1992 | Ness et al. ................... 210/754 |
| 5,858,201 A | * | 1/1999 | Otsuka et al. .............. 205/701 |
| 5,911,909 A | | 6/1999 | Coyle-Rees |
| 6,103,950 A | * | 8/2000 | Rimpler et al. ............. 588/246 |
| 6,162,371 A | * | 12/2000 | Rees et al. ............. 252/187.22 |
| 6,471,974 B1 | * | 10/2002 | Rees et al. ................... 424/405 |

FOREIGN PATENT DOCUMENTS

| JP | 38-6268 B1 | 5/1963 |
| JP | 52-78905 A | 7/1977 |
| JP | 57-61099 | 4/1982 |
| JP | 59-93799 | 5/1984 |
| JP | 59-98200 | 6/1984 |
| JP | 2-111708 A | 4/1990 |
| JP | 4-360672 A | 12/1992 |
| JP | 7233396 A | 9/1995 |
| JP | 7328638 A | 12/1995 |
| JP | 8-164189 A | 6/1996 |
| JP | 9-154922 A | 6/1997 |
| JP | 10-81610 A | 3/1998 |
| JP | 11-49619 A | 2/1999 |
| JP | 11-148097 A | 6/1999 |
| JP | 11-148098 A | 6/1999 |
| JP | 11-188083 A | 7/1999 |
| JP | 11-228316 A | 8/1999 |
| WO | 87/5187 A1 | 9/1987 |
| WO | WO 87/05187 | 9/1987 |
| WO | WO 99/32596 A1 | 7/1999 |

\* cited by examiner

*Primary Examiner*—Joseph D. Anthony
(74) *Attorney, Agent, or Firm*—Birch, Stewart, Kolasch & Birch, LLP

(57) ABSTRACT

The present invention provides a bactericide composition comprising hypochlorous acid or a salt thereof. In particular, the present invention provides a liquid bactericide composition comprising an aqueous solution comprising hypochlorous acid and/or a salt thereof, a surfactant (B) and a pH adjusting agent (C), and having a ph valve in the range of 3 to 8 at 25° C.

16 Claims, No Drawings

MICROBICIDE COMPOSITIONS

This application is the national phase under 35 U.S.C. §371 of PCT International Application No. PCT/JP00/08716 which has an International filing date of Dec. 8, 2000, which designated the United State of America.

TECHNICAL FIELD

The present invention relates to a bactericide composition comprising hypochlorous acid or a salt thereof.

PRIOR ART

Conventionally, chlorine-based germicides such as sodium hypochlorite, calcium hypochlorite and sodium dichloroisocyanurate have been generally used in various environments as germicides and disinfectants. Among them, hypochlorites such as sodium hypochlorite are widely used, since these are advantageous in costs and effects, and there have been many proposals so as to further improve the effects thereof with respect to germicidal action and sterilizing action to microbes that are requested in various fields such as medical and food industries.

For example, JP-A No. 57-61099 has disclosed a liquid germicidal bleaching agent that comprises a hypochlorite, an alkali substance and a specific cationic surfactant of a quaternary ammonium salt type in respectively specific weight ratios.

JP-A No. 7-233396 has disclosed a germicidal washing agent for use in medical equipment such as artificial dialysis devices, which comprises a salt of hypochlorous acid, an alkaline substance and a cationic surfactant of a quaternary ammonium salt at specified weight ratios.

However, although conventional hypochlorite germicides are effective to general bacteria and mold (mycelia) to a certain degree, these fail to provide sufficient effects to virus having higher resistance to medicine, spores formed by rod-shaped bacteria and mold spores in the case of an easy operation.

Moreover, JP-A No. 11-148098 has disclosed a solid-state germicidal detergent containing an alkaline earth metal of hypochlorous acid like high test hypochlorite (calcium hypochlorite). This, however, has not disclosed anything about germicidal processes in a higher degree, and an alkaline earth metal such as calcium causes scales and scum, resulting in degradation in the germicidal effects.

Furthermore, JP-A No. 7-328638 has disclosed a method in which an agent for reducing surface tension is added to electrolytic acidic water so as to increase the adhering property to the outer surface of a germicide-subject substance; however, although this method is superior in the germicidal effects, it generates chlorine gas, causing a problem with safety.

Here, JP-A No. 59-93799 has disclosed a method in which amine oxide is blended in a liquid washing agent comprising a hypochlorite and an alkali substance.

Further, JP-A No. 59-98200 has disclosed a method in which amine oxide is used as a thickener for a bleaching agent comprising a salt of hypochlorous acid; however, these have not described anything about germicidal effects, that is, in particular, germicidal effects to spores and viruses having high resistance.

DISCLOSURE OF INVENTION

The object of the present invention is to obtain a bactericide composition capable of affording a high bactericidal effect while being excellent in safety and workability.

The present invention provides a liquid bactericide composition comprising an aqueous solution with pH (25° C.) of 3 to 8 comprising hypochlorous acid and/or a salt thereof (A), a surfactant (B) and a PH adjusting agent (C).

The present invention also provides a bactericide comprising a product (I) comprising hypochlorous acid and/or a salt thereof (A), a product (II) comprising a surfactant (B) and a product (III) comprising a pH adjusting agent (C), wherein the bactericide is prepared as an aqueous solution comprising (A) and (B) in a weight ratio (A)/(B) of 50/1 to 1/50 in use.

This means that the components (A), (B) and (C) can be used together as an aqueous solution at the time of its use. The aqueous solution preferably has a pH value of 3 to 8 at 25° C. or 20° C. Since the components (A) and (B) are separately preserved and transported until just before use, the bactericide has the excellent stability.

In other words, the present invention provides a method for using a bactericide in which the product (I) comprising hypochlorous acid and/or a salt thereof (A), the product (II) comprising a surfactant (B), and the product (III) comprising a pH adjusting agent (C) are prepared into an aqueous solution comprising (A), (B) and (C) so that the weight ratio of (A)/(B) is in the range of 50/1 to 1/50 just before use.

In this embodiment of use, the components (A), (B) and (C) may be combined as a kit. Alternatively the components (A), (B) and (C) may be, independently of each other, formulated into their respective individual products.

The present invention provides use and a sterilization method of the composition, the aqueous solution and the product kit. The method includes applying effective doses of them to a desired site or location for sterilization.

The preferable surfactant (B) comprises at least one of the surfactants selected from amphoteric surfactants, cationic surfactants and nonionic surfactants. Polyoxyalkylene alkylether and polyoxyalkylene phenyl ether are excluded from the preferable nonionic surfactants. Particularly preferable surfactants are at least one of the surfactants selected from the amphoteric surfactants, cationic surfactants and nonionic surfactant, such as a polyhydric alcohol derivative surfactant. A preferable amphoteric surfactant is an amine oxide.

A pH adjusting agent (C) is preferably an organic acid or a salt thereof, in particular a saturated dibasic acid or a salt thereof.

The ratio (A)/(B) is preferably in the range of 50/1 to 1/50, or 10/1 to 1/10.

The ratio (C)/(A) is preferably in the range of 5/1 to 1/10.

The component (C) may comprise the component (B) before use. In other words, the bactericide according to the present invention comprises a product (IV) comprising hypochlorous acid and/or a salt thereof (A), and a product (V) comprising the surfactant (B) and the pH adjusting agent (C), and is used as an aqueous solution comprising (A) and (B) in a weight ratio (A)/(B) in the range of 50/1 to 1/50.

The bactericide according to the present invention also comprises a product (VI) comprising hypochlorous acid and/or a salt thereof (A) and a surfactant (B), and a product (VII) comprising a pH adjusting agent (C), and is used as an aqueous solution comprising (A) and (B) in a weight ratio (A)/(B) in the range of 50/1 to 1/50.

The bactericide according to the present invention has an antimicrobial effect on viruses and spores formed by bacillus and fungi that are more resistant to chemicals. The bactericide is particularly useful in cleaning, disinfecting and deodorizing. The composition according to the present invention may also comprise a rust preventing agent.

The preferable weight ratio (C) (A) in the aqueous solution is in the range of 2/1 to 1/5, particularly in the range of 1/1 to 1/5.

The preferable weight ratio (A) (B) in the aqueous solution is in the range of 10/1 to 1/10, more preferably in the range of 5/1 to 1/5, and particularly in the range of 5/1 to 1/2 or 2/1 to 1/2. A range of 20/1 to 1/20 is also preferable. More preferably, the range is 20/1 to 1/5, and particularly 20/1 to 1/2. The content of (A) is denoted by a weight ratio based on the amount of available chlorine.

The aqueous solution preferably has a pH range of 3 to 8, more preferably 5 to 8, further preferably 5 to 7, particularly from 5 or more to less than 7, and more particularly from 6 or more and less than 7. The pH value of the solution may be adjusted by the pH adjusting agent that can be selected from an acid, an alkali and a buffering agent. The component (C) may have functions other than a function for adjusting the pH value. The component having such functions include a hydroxide of an alkali metal, a hydroxide of an alkaline earth metal, an inorganic acid or a salt thereof, and an organic acid or a salt thereof. Hydroxides of alkali metals and alkaline earth metals, and organic acids or salts thereof are preferable among them.

The component (C) is used in an amount for adjusting the pH value within the ranges as described above. A pH range of 3 to 8, preferably 5 to 8, more preferably 5 to 7, further preferably 5 or more to less than 7, and particularly 6 or more to less than 7 is recommended especially when the effective concentration of chlorine in the component (A) is adjusted to 125 ppm. A part of the components of the composition may remain undissolved in the aqueous solution as used herein.

The aqueous solution comprising hypochlorous acid (A) can be obtained by a conventional method for producing electrolytic oxidation water, for example by electrolysis of an aqueous solution comprising an electrolyte, or by acid precipitation of a hypochlorite.

The available concentration of chlorine was determined by an "iodometry" according to JIS K-0101 in this invention.

The preferable concentration of (A) in the aqueous solution to be in contact with microorganisms, or the available chlorine concentration is in the range of 5 ppm to 5% by weight, preferably 5 ppm to 1% by weight, particularly 5 to 5000 ppm, more particularly 5 to 1000 ppm, further particularly 5 to 500 ppm, and most preferably 50 to 200 ppm.

The available chlorine concentration may be also in the range of 1 to 5000 ppm, preferably 5 to 2000 ppm.

The components (A), (B) and (C), and the ratio among them are preferably included in the examples in the embodiments to be described hereinafter. One example described in one embodiment may be used as an example in the other embodiment.

Additives other than (A), (B) and (C) described in one embodiment may be used in any embodiments in the present invention. Optional components may be involved in any compositions of the bactericide so long as they do not impair the properties of the product such as stability.

The present invention provides a bactericide composition having a high bactericidal effect, and being excellent in safety and workability.

The microorganisms as objects of the bactericide composition according to the present invention denote common bacteria, fungi, viruses, and spores of fungi and bacteria.

Since the bactericide composition according to the present invention has a wide bactericidal spectrum and is highly effective for not only fungi but also viruses and spores, it is effective for wide range of bactericidal applications.

For example, it may be used for sterilization in hospitals, nursing homes, food processing factories and laundries, as well as sterilization of walls, floors and windows of a kitchen, and furnishings used therein, and for sterilization of vessels, fixture, containers and others (for example bottles of beverage).

While the method for allowing the aqueous solution to contact is not particularly restricted, it include sprinkling, spraying, immersion or filling, and the subject to be sterilized may be wiped with an appropriate carrier impregnated with the aqueous solution. While the contact time of the aqueous solution is also not restricted, a contact time as short as 30 seconds or less, in particular within 10 seconds is sufficient for obtaining desired effects. While the temperature during the contact is not particularly restricted, a temperature rage of 10 to 70° C. is preferable, and a temperature range of 20 to 60° C. is particularly preferable.

The compositions according to the present invention, in particular those in the embodiments T and U to be described hereinafter, are favorable for use in an automatic washer to be used for washing tableware and the like. The automatic washer as used herein denotes an overall apparatus capable of continuous or batch wise washing of hard surfaces of tableware such as cups, and delivery trays such as a plastic container, and the size and washing method are not particularly restricted. Sterilization using the automatic washer is more effective when applied after removing dirt and other contaminants. For example, it is most suitable to spray the composition of the present invention after washing and before final rinsing when the composition is used for a belt conveyer type automatic tableware washer.

Individual component of the composition according to the present invention may be independently delivered and stored before use. Each product may be filled in various packages using glass, metal, plastic and paper in the manufacturing process. The ingredient of the product may be used as it is, or may be used after dilution.

Embodiment R

The embodiment in which the component (B) is an amine oxide and the component (C) is an organic acid or a salt thereof will be described hereinafter.

The present invention relates to a bactericide composition comprising a salt of hypochlorous acid (A) and an amine oxide (B) in a weight ratio (A)/(B) in the range of 10/1 to 1/10 in addition to the organic acid or a salt thereof.

The present invention also relates to a bactericide comprising the product (I) comprising a salt of hypochlorous acid and the product (II) comprising an amine oxide (B), which is prepared as an aqueous solution comprising (A) and (B) in a weight ratio (A)/(B) in the range of 10/1 to 1/10.

The present invention further relates to a bactericide comprising the product (IV) comprising a salt of hypochlorous acid (A) and the product (V) comprising an amine oxide (B) and an organic acid or a salt thereof (C), which is prepared as an aqueous solution comprising (A) and (B) in a weight ratio (A)/(B) in the range of 10/1 to 1/10.

The present invention further relates to a bactericide comprising the product (VI) comprising a salt of hypochlorous acid (A) and an amine oxide (B), and a product (VII) comprising an organic acid or a salt thereof (C), which is prepared as an aqueous solution comprising (A) and (B) in a weight ratio (A)/(B) in the range of 10/1 to 1/10.

While a salt of hypochlorous acid (A) to be used in the present invention includes sodium hypochlorite, potassium hypochlorite and lithium hypochlorite, sodium hypochlorite is preferable among them.

While an amine oxide (B) to be used in the present invention includes alkyldimethyl amine oxide, those having 8 to 18 alkyl groups are preferable.

The bactericide composition according to the present invention comprises a salt of hypochlorous acid (A) and amine oxide (B) in a weight ratio (A)/(B) in the range of 10/1 to 1/10, preferably in the range of 5/1 to 1/5, and more preferably in the range of 2/1 to 1/2.

The proportion of (A) is represented by a weight ratio based on the amount of available chlorine.

It is preferable for the bactericide composition according to the present invention to comprise further an organic acid or a salt thereof (C) in order to improve bactericidal performance. Examples of the organic acid or a salt thereof (C) include a saturated dibasic acid such as malonic acid, succinic acid, glutaric acid, adipic acid, sebacic acid or salts thereof, and an unsaturated dibasic acid such as fumaric acid and maleic acid or salts thereof. The organic acid is preferably a saturated dibasic acid or a salt thereof, more preferably a saturated dibasic acid with a carbon number of 3 to 10 or a salt thereof, and succinic acid or a salt thereof is particularly preferable. The weight ratio (C)/(A) of organic acid or a salt thereof (C) used and a salt of hypochlorous acid (A) is preferably in a range of 5/1 to 1/10, more preferably 2/1 to 1/5, and particularly 1/1 to 1/5.

The bactericide composition according to the present invention may comprise hydroxides of alkali metals and/or hydroxides of alkaline earth metals (D). Examples of (D) include sodium hydroxide, potassium hydroxide and calcium hydroxide, and sodium hydroxide and potassium hydroxide are preferable among them.

The bactericide composition according to the present invention may comprise alkali metal salts of inorganic acids and/or alkaline earth metal salts of inorganic acids (E). Examples of (E) include sodium sulfate, sodium nitrate, sodium carbonate, sodium hydrogen carbonate, magnesium sulfate, magnesium nitrate, magnesium chloride, magnesium carbonate, sodium phosphate, sodium polyphosphate and potassium phosphate. Sodium sulfate, magnesium sulfate, sodium phosphate, sodium polyphosphate and potassium phosphate are preferable among them.

The bactericide composition according to the present invention comprises an aqueous solution comprising the components (A) and (B) in a specified weight ratio. The available chlorine concentration in this aqueous solution is preferably 5 to 5000 ppm, particularly 50 to 200 ppm. The pH value of the aqueous solution (25° C.) is preferably 5 to 12 or 3 to 8, more preferably 5 to 10, further preferably 5 to 8, particularly not less than 5 and less than 7, and more particularly not less than 6 and less than 7. The pH value of the aqueous solution can be adjusted by the organic acid or the salt thereof (C), and with the inorganic acid described above. The amount of each component in the aqueous solution as the bactericide composition according to the present invention is preferably 5 ppm to 12% by weight for the component (A) and 0.5 ppm to 35% by weight for the component (B), and the component (C) is preferably blended in a proportion of 0.5 ppm to 60% by weight. While the aqueous solution is diluted before use, the diluted aqueous solution comprises the component (A) in the range of 5 to 5000 ppm, preferably 10 to 5000 ppm and more preferably 50 to 200 ppm, and the component (B) in the range of 0.5 to 50000 ppm, preferably 5 to 2000 ppm and more preferably 50 to 200 ppm, and the component (C) in the range of 0.5 to 25000 ppm, preferably 5 to 1000 ppm, more preferably 25 to 500 ppm and particularly 25 to 150 ppm. The microorganisms as objects of the bactericide composition according to the present invention include common bacteria, molds, viruses, and spores of fungi and bacteria.

The bactericide according to the present invention comprises the product (I) comprising a salt of hypochlorous acid (A) and product (II) comprising an amine oxide (B), and is prepared as an aqueous solution comprising (A) and (B) in a weight ratio (A)/(B) in the range of 10/1 to 1/10. Optional components may be involved in respective products so long as they do not impair the stability of the products. The bactericide may be also composed of the product (I) and (II) and furthermore other products.

The organic acid or the salt thereof (C) is preferably blended independently from a salt of hypochlorous acid (A), if the former is necessary. An example of the bactericide comprises the product (IV) comprising a salt of hypochlorous acid (A) and the product (V) comprising an amine oxide (B) and an organic acid or a salt thereof (C), wherein an aqueous solution is prepared by mixing the products (IV) and (V) in a weight ratio (A)/(B) in the range of 10/1 to 1/10 before use. The bactericide is preferably prepared as an aqueous solution comprising the components (A) and (C) in a weight ratio (C)/(A) in the range of 5/1 to 1/10, preferably in the range of 2/1 to 1/5, more preferably in the range of 1/1 to 1/5. Another example is a bactericide comprising component (VI) comprising a salt of hypochlorous acid (A) and an amine oxide (B) and the product (VII) comprising an organic acid or a salt thereof (C), wherein the products (VI) and (VII) are mixed as an aqueous solution comprising (A) and (B) in a weight ratio (A)/(B) in the range of 10/1 to 1/10 in use. This bactericide is preferably prepared as an aqueous solution comprising the components (A) and (C) in a weight ratio (C)/(A) in the range of 5/1 to 1/10, particularly in the range of 2/1 to 1/5, and more particularly in the range of 1/1 to 1/5. Optional components may be involved in respective products so long as they do not impair the stability of each component. The bactericide may comprise the products (IV) to (VII) and furthermore other products.

The preferable concentration of each effective ingredient in respective products is 0.1 to 12% by weight of a salt of hypochlorous acid in the product (I), 0.1 to 35% by weight of an amine oxide in the product (II), 0.1 to 12% by weight of a salt of hypochlorous acid in the product (IV), a combined amount of 0.2 to 60% by weight of an amine oxide and an organic acid or a salt thereof in the product (V), a combined amount of 0.2 to 47% by weight of a salt of hypochlorous acid and an amine oxide in the product (VI), and 0.1 to 60% by weight in the product (VII).

The bactericide composition according to the present invention can be prepared by combining the products (I) and (II), the products (IV) and (V), or the products (VI) and (VII) with the product (III).

Embodiment S

The embodiment in which the component (A) is hypochlorous acid will be described hereinafter.

The aqueous solution comprising hypochlorous acid (A) can be obtained by a conventional method for producing electrolytic oxidation water known in the art by, for example, electrolysis of an aqueous solution comprising an electrolyte using permeable membranes, or by acid precipitation of a salt of hypochlorous acid. The concentration of hypochlorous acid (A) in the bactericide composition according to the present invention is preferably 5 ppm to 5% by weight, more preferably 5 ppm to 1% by weight, and particularly 5 ppm to 0.5% by weight, as the available chlorine concentration, which is determined by JIS K-0101 "iodometry").

The pH range (25° C.) of the bactericide composition according to the present invention is 3 to 8, preferably 5 to 8 and more preferably 5 to 7. The pH value is adjusted by the pH adjusting agent (C). The pH adjusting agent serves for maintaining the pH value of the composition according to the present invention in the range of 3 to 8 by adding it, and may be selected from compounds to be used for alkaline reagents and buffer reagents. The pH adjusting agent (C) may have functions other than the pH adjusting function.

The pH adjusting agent (C) comprises a hydroxide of an alkaline metal, a hydroxide of an alkaline earth metal, an inorganic acid or a salt thereof, and an organic acid and a salt thereof. Examples of them include sodium hydroxide, potassium hydroxide, calcium hydroxide, hydrochloric acid, sodium sulfate, sodium nitrate, sodium chloride, sodium carbonate, potassium hydrogen carbonate, sodium hydrogen carbonate, magnesium sulfate, magnesium nitrate, magnesium chloride, magnesium carbonate, trisodium phosphate, tripotassium phosphate, disodium hydrogen phosphate, dipotassium hydrogen phosphate, sodium dihydrogen phosphate, potassium dihydrogen phosphate, sodium polyphosphate, citric acid, sodium citrate, potassium citrate, potassium dihydrogen citrate, potassium hydrogen phthalate and succinic acid. At least one of the reagent selected from sodium hydroxide, potassium hydroxide, hydrochloric acid, sodium sulfate, magnesium sulfate, sodium carbonate, potassium carbonate, sodium hydrogen carbonate, potassium hydrogen carbonate, trisodium phosphate, tripotassium phosphate, disodium hydrogen phosphate, dipotassium hydrogen phosphate, sodium dihydrogen phosphate, potassium dihydrogen phosphate and sodium polyphosphate is preferable among them.

The bactericide composition according to the present invention comprises at least one kind of the surfactant (B). While the surfactant may be selected from the anionic surfactant, cationic surfactant, nonionic surfactant and amphoteric surfactant, those being stable in the aqueous hypochlorous acid solution are used. The cationic surfactant and amphoteric surfactant are preferable among them, and amine oxides are most preferable. Alkyldimethyl amine oxides are preferable as the amine oxide, and those having a carbon number of 8 to 18 are preferable. The ratio (A)/(B) of the surfactant (B) and hypochlorous acid (A) as converted into the available chlorine concentration is preferably 10/1 to 1/10 (in weight ratio), more preferably 5/1 to 1/5, and particularly 5/1 to 1/2.

The bactericide composition according to the present invention may comprise the organic acid (C) or a salt thereof as described in Embodiment R from the view point of improving the bactericidal performance. The organic acid and a salt thereof may also act as a pH adjusting agent.

The bactericide composition according to the present invention may comprise thickeners, perfumes and colorants in addition to the components (A), (B) and (C).

While the bactericide composition according to the present invention is used as a diluted aqueous solution, the concentration of the component (A) as converted into the available chlorine concentration in this diluted aqueous solution is 5 to 5000 ppm, preferably 5 to 1000 ppm, and particularly 5 to 500 ppm.

The sterilization method according to the present invention comprises making microorganisms to contact with an aqueous solution comprising the components (A), (B) and (C) at a pH range (25° C.) of 3 to 8, preferably 5 to 8 and more preferably 5 to 7 with an available chlorine concentration of 5 to 5000 ppm, preferably 5 to 1000 ppm and particularly 5 to 500 ppm. The said microorganisms mean the same as described in the embodiment R.

Embodiment T

The embodiment comprising at least one of the component (A) selected from an alkali metal salt of hypochlorous acid and hypochlorous acid, at least one of the component (B) selected from the cationic surfactant and amphoteric surfactant, and the pH adjusting agent (C), and having a pH range of 3 to 8 at 20° C. will be described hereinafter.

An alkali metal salt of hypochlorous acid is preferable as the component (A). While examples of the alkali metal salt of hypochlorous acid include sodium hypochlorite, potassium hypochlorite and lithium hypochlorite, sodium hypochlorite is preferable. The composition according to the present invention has an available chlorine concentration of preferably 1 to 5000 ppm, more preferably 5 to 1000 ppm and particularly 5 to 500 ppm. It is preferable to use the component (A) so that the available chlorine concentration falls within the range described above.

While the cationic surfactants as the component (B) include primary, secondary and tertiary amines and quaternary ammonium salts, the quaternary ammonium salts are preferable among them. The quaternary ammonium salts have an alkyl or alkenyl group with a total carbon number of 8 to 28 as at least one of the four substituents, and the remaining groups are selected from a benzyl group, an alkyl group with a carbon number of 1 to 5, and a hydroxyalkyl group with a carbon number of 1 to 5. The alkyl or alkenyl group with the total carbon number of 8 to 28 may be substituted with an alkoxy group, an alkenyloxy group, an alkanoylamino group, an alkenoylamino group, an alkanoyloxy group or an alkenoyloxy group with a carbon number within the range described above. The amphoteric surfactants as the component (B) include an amino acid based amphoteric surfactant such as a monoaminocarboxylic acid and polyaminocarboxylic acid, a betaine based amphoteric surfactant such as a N-alkylbetaine, a N-alkylamidobetaine, an N-alkylsulfobetaine, and an imidazoline based amphoteric surfactant such as imidazolinium betaine. The N-alkyl betaine is preferable among them, and the N-alkyl betaine having a carbon number of 12 to 18 is particularly preferable.

The weight ratio (A)/(B) of the composition according to the present invention is preferably 10/1 to 1/10, more preferably 5/1 to 1/5, and particularly 5/1 to 1/2.

Examples of the component (C) include hydroxides of an alkali metal and an alkaline earth metal (D), an inorganic acid and a salt thereof, and an organic acid and a salt thereof. The hydroxides of alkali metals and alkaline earth metals, and the inorganic acids and the salts thereof are those as described in the embodiment R. Other examples include hydrochloric acid, potassium hydrogen carbonate, potassium hydrogen carbonate, trisodium phosphate, tripotassium phosphate, disodium hydrogen phosphate, dipotassium hydrogen phosphate, sodium dihydrogen phosphate and potassium dihydrogen phosphate. The organic acids and the salts thereof are also those described in the Embodiment R.

The composition according to the present invention preferably has a pH value in the range of 3 to 8, more preferably in the range of 5 to 8, and particularly in the range of 5 to 7 at 20° C. The component (C) is preferably used in an amount so that the pH value falls within this range.

The composition according to the present invention is also able to have a stable blend with hypochlorous acid and/or a salt thereof, and an anionic surfactant (F) may be comprised for enhancing the washing effect. The component (F) include salts of higher fatty acid, sulfuric acid esters of higher alcohol, sulfonic acid esters of higher alcohol, fatty acid sulfate, fatty acid sulfonate, phosphate ester, sulfate esters of fatty acid ester, sulfonate esters of fatty acid esters, sulfate esters of higher alcohol ether, sulfonate esters of higher alcoholic ether, acetate substituted with higher alcohol ethers, condensates of fatty acid and amino acid, alkylol sulfate esters of fatty acid amide, alkylsulfonates of fatty acid amide, sulfosuccinic acid ester, alkylbenzene sulfonate, alkylphenol sulfonate, alkylnaphthalene sulfonate, alkylbenzoimidazole sulfonate, amido ether carboxylic acid or salts thereof, ether carboxylic acid or salts thereof, N-acyl-N-methylamine or salts thereof, amidoether sulfate or salts thereof, N-acylglutamic acid or salts thereof, N-amidoethyl-N-hydroxyethyl acetic acid or salts thereof, acyloxyethane sulfonic acid or salts thereof, N-acyl-β-alanine or salts thereof, N-acyl-N-carboxyethyl taurine or salts thereof, N-acyl-N-carboxyethylglycine or salts thereof, and alkyl or alkenyl aminocarbonylmethyl sulfuric acid or salts thereof. The amount of blending of the component (F) is preferably not more than 10 times, more preferably not more than 5 times, and particularly not more than 2 times in weight ratio relative to the component (B).

Embodiment U

The embodiment in which the component (B) is a polyhydric alcohol derivative surfactant will be described hereinafter. The component (A) that exhibits the bactericidal effect preferably comprises hypochlorous acid or salts hereof, and alkali metal salts of hypochlorous acid is preferable among them. While examples of the alkali metal salts of hypochlorous acid include sodium hypochlorite, potassium hypochlorite and lithium hypochlorite, sodium hypochlorite is preferable.

Examples of the component (B) that improves wettability include glycerin fatty acid esters, polygycerin fatty acid esters, propyleneglycol fatty acid esters, polypropyleneglycol fatty acid esters, sucrose fatty acid esters, sorbitan fatty acid esters and alkylpolyglycoside et al. The carbon number at the fatty acid moiety of the various fatty acid esters above is preferably 6 to 24, and more preferably 6 to 18. The component (B) preferably comprises polygycerin (preferably with a degree of condensation of 2 to 50) fatty acid (preferably with a carbon number of 6 to 24) esters and alkyl (preferably with a carbon number of 6 to 24) polyglycoside.

The weight ratio (A)/(B) of the components (A) and (B) composition according to the present invention is preferably 1/50 to 50/1, more preferably 20/1 to 1/20, more preferably 20/1 to 1/5, and particularly 20/1 to 1/2.

While the organic acid or the salt thereof as the component (C) is as described in the Embodiment R, examples of them include citric acid, acetic acid, lactic acid, malic acid, tartaric acid and glucuronic acid, succinic acid or a salt thereof is particularly preferable from the view point of the stability of the formulation.

The component (C) is preferably selected from at least one acid and a salt thereof described in The Standard of Food Additives. The component (C) is also preferably selected from at least one acid having carboxyl groups and a salt thereof. The component (A) is distinguished from the component (C).

The pH of the aqueous solution comprising an available chlorine concentration of 125 ppm at 20° C. is 3 to 8, preferably 5 to 8, more preferably 5 to 7, and particularly not less than 6 and less than 7. The component (C) is preferably comprised so that the pH of the solution falls within the range described above. The aqueous solution as used herein include those in which a part of the components remains undissolved.

The composition according to the present invention is used so that the available chlorine concentration is in the range of 1 to 5000 ppm, preferably 5 to 2000 ppm, and particularly 5 to 1000 ppm.

The composition of the present invention may form a stable blending with hypochlorous acid or a salt thereof, and may comprise an anionic surfactant (F) (referred as the component (F) hereinafter) in order to enhance washing effect. The blended amount of the component (F) is preferably not more than 10 times, more preferably not more than 5 times or particularly not more than twice, by weight as much as the component (B).

The bactericide according to the present invention comprises the product (I) comprising the component (A), the product (II) comprising the component (B), and the product (III) comprising the component (C), and is used as an aqueous solution comprising the components (A) (B) and (C) together preferably with an available chlorine concentration of 1 to 5000 ppm.

In another embodiment, the bactericide according to the present invention comprises the product (IV) comprising the component (A), and the product (V) comprising the components (B) and (C), and is used as an aqueous solution comprising the components (A), (B) and (C) together preferably with an available chlorine concentration of 1 to 5000 ppm.

Optional components may be comprised in each product in any of the foregoing bactericides, so long as the additive does not impair the stability of the product. The bactericide may comprise the products (I), (II) and (III), or the products (IV) and (V), and furthermore any products other than them.

The products (I) and (IV) preferably comprise the component (A) as an effective ingredient in a concentration of 0.1 to 12% by weight, the products (II) and (V) preferably comprise the component (B) as an effective ingredient in a concentration of 0.1 to 30% by weight, and the products (III) and (V) preferably comprises the pH adjusting agent in a concentration of 0.1 to 30% by weight. It is preferable for the product to comprise the components (A) and (B) so that the weight ratio (A)/(B) falls within the range of 1/50 to 50/1. The aqueous solution comprising available chlorine concentration of 125 ppm preferably shows a pH value in the range of 3 to 8 at 20° C.

The bactericide composition according to the present invention can be prepared from the products (I) (II) and (III), or from the products (IV) and (V).

Embodiment V

The present invention is effective as a washing agent composition.

The washing agent is used as an aqueous solution comprising the components (A) and (B) in a weight ratio (A)/(B) of 10/1 to 1/10.

The washing agent according to the present invention comprises the product (I) comprising hypochlorous acid (A) and the product (II) comprising amine oxide (B), and is used as an aqueous solution comprising the components (A) and (B) in a weight ratio (A)/(B) of 10/1 to 1/10. Optional components may be comprised in each product so long as they do not impair the stability of the product. The washing agent may comprise the products (I) and (II) as well as any products other than them.

When an organic acid or a salt thereof (C) is used, it is preferably blended independently from hypochlorous acid (A). In particular, the washing agent comprises the product (IV) comprising hypochlorous acid (A), amine oxide (B) and an organic acid or a salt thereof (C), and is used as an aqueous solution comprising the components (A) and (B) in a weight ratio (A)/(B) in the range of 10/1 to 1/10. The washing agent also comprises the product (VI) comprising hypochlorous acid (A) and amine oxide (B) and the product (VII) comprising an organic acid or a salt thereof (C), and is used as an aqueous solution comprising the components (A) and (B) in a weight ratio (A)/(B) in the range of 10/1 to 1/10. Optional components may be comprised in each product, so long as they do not impair the stability of the product. The washing agent may comprise the products (IV) to (VII), and furthermore any products other than them.

The concentrations of the effective ingredients in each product are: 0.1 to 12% by weight of hypochlorous acid in the product (I); 0.1 to 35% by weight of amine oxide in the product (II); 0.1 to 12% by weight of hypochlorous acid in the product (IV); a combined proportion of amine oxide and an organic acid or a salt thereof of 0.2 to 60% by weight in the product (V); a combined proportion of hypochlorous acid and amine oxide of 0.2 to 47% by weight in the product (VII).

The washing agent composition according to the present invention can be prepared from the components (I), (II) and (III), or from the components (IV) and (V), or from the components (VI) and (VII).

The present invention provides a washing agent composition having a high detergency against oil stain at around a neutral pH, while being excellent in safety and workability. It has been generally recognized that the detergency is higher at an alkaline pH. However, since the reduction-oxidation potential of hypochlorous acid is higher at the neutral region than at the alkaline region with respect to the composition according to the present invention, the detergency is not reduced at the safer neutral region.

Embodiment W

The present invention provides a deodorant composition that exhibit an excellent deodorant effect against all bad smell generating at a toilet, kitchen, boot cupboard, bathroom, and sheets in theaters and movie halls.

The present invention relates to a deodorant composition comprising at least one of the composition (A) selected from hypochlorite and hypochlorous acid, at least one of the composition (B) selected from the amphoteric surfactant and cationic surfactant, and the pH adjusting agent (C).

The present invention also relates to a spray type deodorant filled in a vessel having a hand type sprayer, wherein the components (A) and (C) are separately retained in the vessel, the component (B) is stored together with at least one of the components (A) and (C), and the components (A), (B) and (C) are mixed together by spraying.

The present invention provides a deodorant composition that can exhibit a high deodorant effect by using a small amount of it with a high odor extinguishing rate.

The deodorant composition according to the present invention may be used in various forms by, for example, impregnating a carrier such as a gel and porous material with the composition, by filling a spray bottle (trigger type and dispenser type bottles) with the composition, by forming an aerosol, or by allowing the composition to evaporate by a capillary effect after sucking the composition up into a wick inserted into the composition that has been filled in a vessel.

Embodiment X

The present invention provides a bactericidal space cleaning composition comprising at least one of the component (A) selected from hypochlorite and hypochlorous acid, at least one of the component (B) selected from the amphoteric surfactant and cationic surfactant, and the pH adjusting agent (C).

The present invention also provides a method for sterilizing and cleaning the space by discharging the bactericidal space cleaning composition according to the present invention as a foam or mist.

An excellent bactericidal and washing effect of the space may be obtained by discharging the bactericidal space cleaning composition according to the present invention as a form or mist. The space as used herein include spaces in hospital, nursing homes, food manufacturing factory, kitchen and toilet, and the size and shape of the space is not particularly restricted.

Embodiment Y

The present invention provides a bactericide composition comprising at least one of the component (A) selected from hypochlorous acid and alkali metal salts of hypochlorous acid, at least one of the component (B) selected from the cationic surfactant and amphoteric surfactant, at least one of the component (C) selected from organic acids and salts thereof, and a rust preventive agent as a component (G).

The component (G) preferably comprises at least one of the acids or salts selected from phosphoric acid, polyphosphoric acid, sulfonic acid and salts thereof, and the preferable salts include alkali metal salts such as sodium salts and potassium salts. The component (G) is preferably used so that the weight ratio (A)/(G) relative to the components (A) is 10/1 to 1/10, more preferably 10/1 to 1/5, and particularly 5/1 to 1/5.

EXAMPLES

All the deposited strains of microorganism used in the examples below is obtained from The Institute for Fermentation, OSAKA, IFO located at 2-17-85, Juso-Honmachi, Yodogawa-ku, Osaka, Japan, which is described in Microorganisms 10$^{th}$ List of Culture, 1996. Examples R1 to R6 and Comparative Examples R1 to R3

The following experiments were performed using the aqueous solutions shown in Table R1. The results are listed in Table R1.

The blended composition used in Example R1 was obtained by mixing aqueous solutions of sodium hypochlorite (available chlorine concentration 60,000 ppm) and amine oxide (effective ingredient 35%), wherein each solution was diluted twice with ion-exchanged water to a final concentration, and an equal volume each of the diluted solutions were mixed together. For obtaining the blended compositions used in Examples R2 to R4, a solution was prepared by mixing aqueous solutions of sodium hypochlorite (available chlorine concentration 60,000 ppm) and amine oxide in a prescribed mixing ratio, the mixed solution was diluted twice with ion-exchanged water to a final concentration, and the diluted solution was mixed with an equal volume of an aqueous solution of succinic acid prepared by diluting twice with ion exchanged water to a final concentration. For obtaining the blended compositions used in Examples R5 and R6, an aqueous solution of sodium hypochlorite (available chlorine concentration 60,000 ppm) was diluted twice with ion-exchanged water to a final concentration, a mixed aqueous solution of amine oxide and succinic acid solutions in a prescribed ratio was diluted twice with ion exchanged water to a final concentration, and an equal volume each of both diluted solutions were mixed together.

[R1] Sporicide Test

Spores of (1) *Bacillus cereus* IFO 13494 and (2) *Bacillus subtilis* ATCC 6051 obtained at the heat-treatment by a conventional method to subject the spores to a test. Precultured cells on a SCD agar medium (made by Nihon Pharmaceutical Ind. Co.) were scratched up with a loop. The sampled cells were dispersed in 1 ml of sterilized water, heat treated at 65° C. for 30 minutes followed by washing twice with a centrifuge to subject the cells to the test.

A 0.1 ml aliquot of the solution of the spores for the test (about $10^9$ to $10^{10}$ cells/ml) was sampled. After allowing the sampled cells to contact 10 ml of an aqueous solution, prepared by diluting each aqueous solution comprising the components in Table R1 with sterilized ion-exchanged water, for 10 seconds at 25° C., a 50 μl aliquot of the suspension was sampled and inoculated on a micro-plate (made by CORNING Co., 96-cell wells) comprising 0.2 ml of a post-culture SCD LP medium (comprising 3.3% of sodium thiosulfate). After incubation at 30° C. for 48 hours, growth of the microorganisms on the micro-plate was observed to determine the minimum dilution ratio (the minimum bactericidal available chlorine concentration) where no growth of the microorganisms was observed. The available chlorine concentration was determined by "iodometry" according to JIS K-0101.

[R2] Moldicide Test

Molds (fungi, *Aspergillus niger* IFO6341) were cultured for 7 days at 25° C. using a PDA medium. After homogenizing the cells obtained by a glass beads method, foreign substances were eliminated by a sheet of sterilized gauze to obtain a fungus suspension. A 0.1 ml aliquot of this fungus suspension (about $10^9$ to $10^{10}$ cells/ml) was sampled. After allowing the sampled cells to contact 10 ml of an aqueous solution, prepared by diluting an aqueous solution comprising the component in Table R1 with ion-exchanged water at a dilution rate shown in Table R1, for 10 seconds at 25° C., a 0.1 ml aliquot of the test suspension was sampled and inoculated on a post-culture PDA medium (comprising 3.3% of sodium thiosulfate). Growth of the microorganisms cultured for 7 days at 25° C. was observed by the naked eye, and was evaluated as described above.

TABLE R1

|  |  | Example | | | | | | Comparative example | | |
|---|---|---|---|---|---|---|---|---|---|---|
|  |  | R1 | R2 | R3 | R4 | R5 | R6 | R1 | R2 | R3 |
| Blended components (weight %) | | | | | | | | | | |
| (A) | Sodium hypochlorite[(1)] | 1.05 (1) | 1.05 (1) | 0.525 (0.5) | 1.05 (1) | 1.05 (1) | 1.05 (1) | 1.05 (1) | 1.05 (1) | 1.05 (1) |
| (B) | Lauryl dimethylamine oxide[(2)] | 2 | 2 | 0.25 | | 2 | | 0.05 | | |
|  | Myristyl dimethylamine oxide | | | | 1 | | 1 | | | |
| Polyoxyethylene laurylether sulfate[(3)] | | | | | | | | | | 1 |
| (C) | Succinic acid | | 0.5 | 0.4 | 0.5 | 0.85 | 0.85 | | 0.5 | |
| Hydrochloric acid | | 0.5 | | | | | | | | |
| Water | | Balance | Balance | Balance | Balance | Balance | Balance | Balance | Balance | Balance |
| Total | | 100 | 100 | 100 | 100 | 100 | 100 | 100 | 100 | 100 |
| pH after diluting to 200 ppm (25° C.) | | 6.5 | 6.8 | 6.5 | 6.8 | 6.5 | 6.5 | 11 | 6.8 | 11 |
| Weight ratio (A)/(B) | | 1/2 | 1/2 | 2/1 | 1/1 | 1/2 | 1/1 | 20/1 | — | — |
| Weight ratio (C)/(A) | | — | 1/2 | 4/5 | 1/2 | 4.3/5 | 4.3/5 | — | 1/2 | — |
| Minimum bactericidal available chlorine concentration ppm) | Bacillus cereus | 150 | 125 | 80 | 100 | 60 | 50 | 3000 | 1500 | 3000 |
|  | Bacillus subtilis | 300 | 250 | 100 | 200 | 80 | 70 | 5000 | 2000 | 5000 |
|  | Fungus | 150 | 125 | 50 | 100 | 60 | 50 | 2000 | 1500 | 3000 |

[(1)]The figure in the parenthesis denotes the available chlorine concentration in water before dilution
[(2)]Amphitol 20N (made by Kao Corp., effective concentration 35%)
[(3)]Mean moles of addition of ethylene oxide: 3 moles, sodium salt

Examples R7 to R10

An aqueous solution comprising the components in Table R2 is diluted with ion-exchanged water in a dilution ratio shown in Table R2 to prepare the test aqueous solution comprising (available chlorine concentration 200 ppm). After sealing the solution in a sample bottle, it was stored in a constant temperature chamber at 40° C. for 2 days. An aqueous solution of sodium hypochlorite (available chlorine concentration 60,000 ppm) was diluted twice with ion-exchanged water to a final concentration, and an aqueous solution prepared mixing amine oxide and an organic acid in a prescribed mixing ratio was diluted twice with ion exchanged water to a final concentration. The test solution was obtained by mixing an equal volume each of both aqueous solutions.

The sample bottle was taken out of the chamber 2 days after, and the available chlorine concentration in the test aqueous solution was measured. The retention ratio (%) of the available chlorine concentration was determined by the following equation. The results are shown in Table R2.

Retention ratio (%) = [available chlorine concentration after 2 days' preservation at 40° C./200] × 100

TABLE R2

|  |  | Example | | | |
|---|---|---|---|---|---|
|  |  | R7 | R8 | R9 | R10 |
| Blended components in aqueous solution (% by weight) | | | | | |
| (A) | Sodium hypochlorite [figures in parenthesis denotes the available chlorine concentration of aqueous solution] | 1.05 (1) | 1.05 (1) | 1.05 (1) | 1.05 (1) |
| (B) | Lauryl dimethylamine oxide* | 1 | 1 | 1 | 1 |
| (C) | Succinic acid | 0.4 | | 0.85 | |
|  | Fumaric acid | | 0.3 | | 0.65 |
| Water | | Balance | Balance | Balance | Balance |
| Total | | 100 | 100 | 100 | 100 |
| Weight ratio (A)/(B) | | 1/1 | 1/1 | 1/1 | 1/1 |
| Weight ratio (C)/(A) | | 2/5 | 3/10 | 4.3/5 | 3.3/5 |
| Test solution | Dilution ratio of aqueous solution | 50 | 50 | 50 | 50 |
|  | Effective chlorine concentration (ppm) | 200 | 200 | 200 | 200 |
|  | pH | 7 | 7 | 6.5 | 6.5 |
| Stability on storage | Retention ratio (%) of effective chlwrine concentration | 80 | 45 | 75 | 40 |

*Amphitol 20N (made by Kao Corp., effective ingredient 35%)

Examples S1 to S3 and Comparative Examples S1

Aqueous hypochlorous acid solution (pH 2.7 at 25° C., available chlorine concentration 50 ppm) generated at the anode side of the so-called electrolysis oxidation water obtained by a diaphragm membrane method was used to prepare a bactericide composition by the method described below. The concentration of hypochlorous acid was determined from the available chlorine concentration measured by "the iodometry" according to JIS K-0101.

(1) A bactericide composition is obtained by adjusting the hypochlorous acid solution at pH 5 or pH 11 (comparative example) with an aqueous solution of 0.1 mole/L sodium hydroxide (Example S1).

(2) A bactericide composition is obtained by adjusting the hypochlorous acid solution at pH 6 with an aqueous solution of 0.1 mole/L sodium hydroxide, followed by adding lauryl dimethylamine oxide at a concentration of 25 ppm (Example S2).

(3) A bactericide composition is obtained by adjusting the hypochlorous acid solution at pH 5 with a 0.1 mol/L potassium dihydrogen phosphate/disodium hydrogen phosphate buffer at pH 7 (Example S3).

The following tests were performed using each bactericide composition. The test results are shown in Table S1. Generation of chlorine gas from each bactericide composition was suppressed to a low level that arises no safety problems.

[S1] Sporicide Test

After culturing spores of Bacillus subtilis ATCC 6633 on a SDC agar medium (made by Nihon Pharmaceutical Industry Co.) for 50 days at 30° C., the cells obtained was washed twice by centrifugation followed by a heat treatment at 65° C. for 30 minutes to prepare a spore suspension ($10^5$ cells/ml). A 50 µl aliquot of the spore suspension was injected in 2 ml of the bactericide composition. After incubation at room temperature for 5 minutes, a 50 µl aliquot of the cell contact was sampled, and was seeded on a micro-plate (made by CORNING Co., 96-cell wells) filled with 0.2 ml of post-culture SCDLP medium (comprising 3.3% of sodium thiosulfate). After 48 hours' culture at 30° C., growth of the cells was observed by naked eye to confirm growth of the cells on the micro-plate. The wells with grown cells were evaluated as ⊙ and without grown cells as ×.

[S2] Moldicide Test

A cell suspension ($10^5$ cells/ml) was obtained by the same method as in Test R, except that the culture duration time was set at 30 days.

A 50 µl aliquot of this suspension was injected into 2 ml of the bactericide composition and, after allowing the cell to contact the composition, a 0.1 ml aliquot of the cell contact solution was sampled and seeded on a post-culture PDA medium (comprising 3.3% of sodium thiosulfate). After 7 days' culture at 25° C., growth of fungi was observed by naked eye to evaluate as described above.

TABLE S1

|  | Example | | | Comparative example |
|---|---|---|---|---|
|  | S1 | S2 | S3 | S1 |
| Comparison in Bactericide composition | | | | |
| Hypochlorous acid (as available chlorine concentration) | 50 ppm | 50 ppm | 50 ppm | 50 ppm[1] |
| Sodium hydroxide | pH adjustable amount | pH adjustable amount | — | PH Adjustable amount |
| Potassium dihydrogen Phosphate/disodium hydrogen phosphate buffer | — | — | pH adjustable amount | — |
| Lauryl dimethylamine oxide | — | 25 ppm | — | — |
| Water | Balance | Balance | Balance | Balance |
| pH | 5 | 6 | 7 | 11 |
| Bactericidal activity   Bacillus subtilis ATCC6633 | ⊙ | ⊙ | ⊙ | x |
| Aspergillus niger IFO6341 | ⊙ | ⊙ | ⊙ | x |

[1])Exist as a salt

Examples T1 to T6 and Comparative Examples T1 to T3

The following tests were performed using the compositions comprising the components shown in Table T1, and the results are shown in Table T1. The available chlorine concentration in Table T1 was measured by the "iodometry" according to JIS K-0101.

An aqueous solution was prepared by diluting an aqueous solution, obtained by mixing an aqueous solution of sodium hypochlorite (available chlorine concentration 60,000 ppm) and the component (B) and/or (C) in a prescribed mixing ratio, twice with ion-exchanged water to a final concentration, and another aqueous solution was prepared by diluting a succinic acid solution twice with ion exchanged water to a final concentration. Each composition was obtained by mixing an equal volume each of the above solutions.

These compositions were diluted to the available chlorine concentrations in Table T1 to prepare the aqueous test solutions, which were used for the bactericidal activity and detergency tests. The results are shown in Table T1.

[T1] Bactericidal Activity

[T1-1] Sporicide Test

Bacillus subtilis ATCC 6633 and Bacillus cereus IFO 13494 as spore forming bacteria after pre-culture on the SCD agar medium (made by Nihon Pharmaceutical Industry Co.) were scratched up with a platinum loop. The sampled bacteria were suspended in 1 ml each of water, and washed twice by centrifugation after a heat treatment to subject the cells to the test (cell concentration $10^{10}$ cells/ml in both samples).

A 0.1 ml aliquot of each test spore suspension was seeded in an aqueous solution (25° C.) prepared by diluting each composition comprising the components in Table T1 with sterilized ion-exchanged water, followed by allowing the test cells to contact the aqueous solution for 3 minutes at room temperature. A 50 μl aliquot of the cell contact suspension was sampled within 10 seconds, and was seeded on a micro-plate (made by CORNING Co., 96-cell wells) filled with 0.2 ml of a post-culture SCDLP medium (comprising 3.3% sodium thiosulfate). After 48 hours' culture at 30° C., growth of the cells was observed by naked eye to confirm whether the cells had grown on the micro-plate, and the minimum dilution ratio where no growth of the cells was observed (the minimum bactericidal available chlorine concentration) was determined. The available chlorine concentration was measured by the "iodometry" according to JIS K-1010.

[T1-2] Moldicide Test

Molds (fungi, *Aspergillus niger* IFO 6341) as a test organism were cultured for 7 days at 25° C. using the PDA medium. After homogenizing the cells obtained using a glass beads method, foreign substances were removed using a sheet of sterilized gauze to obtain a cell suspension (with a concentration about $10^5$ cells/ml). A 0.1 ml aliquot of this cell suspension was sampled, and seeded in an aqueous solution (25° C.) prepared by diluting each composition in Table T1 with sterilized ion-exchanged water. After allowing the cells to contact each composition for 10 seconds at room temperature, a 0.1 ml aliquot of the suspension was sampled, which was seeded on a post-culture medium (comprising 3.3% of sodium thiosulfate). After 7 days' culture at 25° C., growth of the cell was observed by naked eye to evaluate as described above.

[T2] Detergency

Models of stain by oil and protein were prepared, and detergency for each stain was evaluated by a modified Leenerts test method

[T2-1] Detergency for Oil Stains

Twenty grams of an oil stain solution is prepared by dissolving a mixed oil and fat prepared by mixing a tallow and 20 g of soy bean oil in 1:1 volume ratio, 0.25 g of monoolein, and 0.1 g of oil red in 60 ml of chloroform. Each weight of glass plates in a group comprising six plates of clean slide glasses is measured to a digit of 1 mg. The slide glasses are dipped into the oil stain solution at 25±1° C. one by one to a depth of about 55 mm for about 2 seconds, and are taken out after allowing stain to adhere. A mass of stain adhered at the lower end of each slide glass are absorbed using a sheet of cloth such as gaze or filter paper, and the weight of each slide glass on which the oil stain are uniformly adhered is measured after drying it in the air at 25±1° C. The amount of the adhered oil stains is adjusted to be within 0.140±0.010 g per six plates of the stain model glass pieces. After allowing the stain model glass plate to dry in the air, it is used for a detergency test within a period of not less than 1 hour and not more than 2 hours after the preparation.

The detergency test was performed as follows. Six groups of the stain model glass plates are washed at 25±2° C. for five minutes using a Leenerts modified washing machine, and are rinsed with ion-exchanged water at 25±2° C. for 30 seconds. The glass plates after completing rinsing are allowed to dry in the air for 24 hours. The detergency is evaluated by measuring the weight of the model stain glass before and after washing. The detergency (%) is calculated from the weight difference before and after washing by the following equation:

Detergency(%)=[(weight before washing−weight after washing)/amount of adhered oil stain]×100

Each detergency for each of the six glass plates is calculated, and the detergency of the composition was determined from the mean value of the detergency of the four glass plates after excluding the maximum and minimum detergency from the six glass plates.

[T2-2] Detergency for Protein Stain

A protein stain solution with a total weight of 100 g is prepared by dissolving and diluting 20 g of skim milk powder in ion-exchanged water at 60° C. A group of clean slide glasses are dipped in the protein stain solution one by one at 25° C.±1° C. to a depth of 55 mm, and taken out after allowing protein stain to adhere. A mass of stain adhered at the lower end of the slide glass are absorbed using a cloth such as a sheet of gauze or a sheet of filter paper, and the slide glass is air-dried at 25±1° C. after allowing protein stain to uniformly adhere on the glass. This procedure is repeated one more and, after completely removing the stain adhered on one surface of the slide glass, the adhered protein is denatured by drying at 110° C. in the air for 1 hour to prepare a test piece. The test piece is subjected to the test within a period of not less than 12 hours and not more than 24 hours after the preparation. The test piece is washed at 25° C.±2° C. for 5 minutes using a Leenerts modified washing machine, and is rinsed with ion-exchanged water for 30 seconds at 25° C.±2° C. The test piece is dried at 70° C. for 30 minutes after rinsing. After drying at 70° C. for 30 minutes after rinsing and staining the test piece with 1% erythrosine solution, the colored surface area ($S_1$) by photographic judgment, and the detergency (%) is calculated by the following equation using the initial area ($S_0$) of the adhered protein stain before washing.

Detergency(%)=[($S_0$−$S_1$)/$S_0$]×100

The detergency is calculated for each of the six glass plates, and the detergency of the composition was determined from a mean value of four detergency after excluding the maximum and minimum values of the six detergency.

TABLE T1

| | Example | | | | | | Comparative example | | |
|---|---|---|---|---|---|---|---|---|---|
| | T1 | T2 | T3 | T4 | T5 | T6 | T1 | T2 | T3 |
| Bactericidal composition Blended components | | | | | | | | | |
| (A) Sodium hypochlorite[1] | 1.05 | 1.05 | 1.05 | 1.05 | 1.05 | 1.05 | 1.05 | 1.05 | 1.05 |
| | (1) | (1) | (1) | (1) | (1) | (1) | (1) | (1) | (1) |
| (B) Quaternary ammonium salt[2] | 1 | 1 | | | | | | | |
| Benzalkonium chloride[3] | | | 1 | 1 | 1 | | | | |
| Lauryldimethylamino acetic acid betaine[4] | | | | | | | 1 | | |

TABLE T1-continued

|  |  | Example | | | | | | Comparative example | | |
|---|---|---|---|---|---|---|---|---|---|---|
|  |  | T1 | T2 | T3 | T4 | T5 | T6 | T1 | T2 | T3 |
| (C) Succinic acid | | 0.85 | 1 | 1.75 | 0.85 | 0.85 | 0.85 |  | 0.85 |  |
| (F) Polyoxyethylene laurylether sulfate[5] | | | | | | 0.2 | | | | |
| Polyoxyethylene laurylether[6] | | | | | | | | | | 1 |
| Water | | Balance | Balance | Balance | Balance | Balance | Balance | Balance | Balance | Balance |
| Total | | 100 | 100 | 100 | 100 | 100 | 100 | 100 | 100 | 100 |
| Bactericidal washing test | | | | | | | | | | |
| Test solution | Available chlorine concentration (ppm) | 500 | 500 | 500 | 500 | 500 | 500 | 500 | 500 | 500 |
|  | pH (20° C.) | 6.5 | 6 | 5 | 6.5 | 6.5 | 6.5 | 11 | 6.5 | 11 |
| Bactericidal activity | Minimum bactericidal activity (ppm) Bacillus subtilis | 150 | 120 | 120 | 150 | 150 | 200 | 6000 | 1500 | 6000 |
|  | Bacillus cereus | 120 | 100 | 100 | 150 | 150 | 200 | 5000 | 2000 | 5000 |
|  | Fungi | 100 | 80 | 100 | 120 | 120 | 150 | 3000 | 1000 | 3000 |
| Detergency | Detergency of oil stain (%) | 46 | 47 | 47 | 45 | 46 | 43 | 15 | 23 | 25 |
|  | Detergency of protein stain (%) | 42 | 42 | 41 | 40 | 42 | 40 | 12 | 21 | 20 |

[1]The figure in the parenthesis denotes the available chlorine concentration.
[2]The available chlorine concentration was adjusted to the values in Table T1 using Quartamin D10P (made by Kao Corp., effective ingredient 75%).
[3]The available chlorine concentration was adjusted to the values in Table T1 using Sanisol C (made by Kao Corp., effective ingredient 50%).
[4]The available chlorine concentration was adjusted to the values in Table T1 using Amphitol 24B (made by Kao Corp., effective ingredient 26%).
[5]The available chlorine concentration was adjusted to the values in Table T1 using Emal 20C (made by Kao Corp., effective ingredient 25%).
[6]The available chlorine concentration was adjusted to the values in Table T1 using Emulgen 106 (made by Kao Corp.).

Example T7

Comparative Example T4

The composition of Comparative Example T4 in Table T2 was obtained using an aqueous hypochlorous acid solution (pH 2.7 at 25° C., available chlorine concentration 50 ppm) generated at the anode side of the so-called electrolytic oxidation water obtained by a diaphragm membrane method, and by adjusting the solution to pH 11 with an aqueous sodium hydroxide solution at a concentration of 1 mole/L. The composition of Example T7 was also obtained by adjusting the same aqueous hypochlorous acid solution to pH 5 with an aqueous solution of disodium succinate with a concentration of 1 mole/L, followed by adding quaternary ammonium salt (Quartamin D10P, the same compound as used in Example T1) to be a concentration of 50 ppm. Bactericidal activity was tested by the same method as in Example T1 using the compositions described above. The bactericidal activity was evaluated as ⊚ or ˣ in accordance with the presence or absence of growth of the microorganisms, respectively. The test results are listed in Table T2.

TABLE T2

|  |  | Example T7 | Comparative example T4 |
|---|---|---|---|
| Blended components | | | |
| (A) | Hypochlorous acid | 50 ppm | 50 ppm |
| (B) | Quarternary ammonium salt | 50 ppm | — |
| (C) | Disodium succinate | pH adjustable amount | — |
|  | Sodium hydroxide | — | pH adjustable amount |
| Available chlorine concentration in bactericidal washing | | 50 ppm | 50 ppm |

TABLE T2-continued

|  | Example T7 | Comparative example T4 |
|---|---|---|
| solution (ppm) | | |
| pH (20° C.) | 5 | 11 |
| Bactericidal activity | | |
| Bacillus subtilis | ⊚ | x |
| Bacillus Cereus | ⊚ | x |
| Fungi | ⊚ | x |

Example U1 to U20 and Comparative Example U1 to U4

The following tests were performed using the diluted aqueous solutions (test aqueous solutions) comprising the compositions shown in Tables U1 and U2. The available chlorine concentration in Tables U1 and U2 was measured by the "iodometry" according to JIS K0101.

An equal volume of each of the component (A) and (B) were mixed and, the mixture was diluted twice with ion-exchanged water to the final concentration. The component (C) was also diluted twice with ion exchanged water to the final concentration. An equal volume of these diluted solutions were mixed to prepare the test solutions having the available chlorine concentration shown in Tables U1 and U2. The bactericidal activity was tested using these test solutions. The results are shown in Tables U1 and U2. The compositions in Examples U1 to U16, U19 and U20, and in Comparative Examples U1 to U4 in the aqueous solution with an available chlorine concentration of 125 ppm had the same pH value (20° C.) as that in the test aqueous solutions in Tables U1 and U2 with an available chlorine concentration of 1000 ppm.

[U1-1] Sporicide Test

Bacillus subtilis ATCC 6633 and Bacillus cereus IFO 13494 were pre-cultivated on the SCD agar medium (made by Nihon Pharmaceutical Industry Co.). Cultured cell were scratched up with a loop, and suspended in 1 ml of sterilized water. After the heat-treatment at 65° C. for 30 minutes, the cells were washed twice by centrifugation, and were used for the test (cell concentration $10^5$ cells/ml).

A 0.1 ml aliquot of the test solution was sampled, and was injected into 10 ml of an aqueous solution (25° C.) prepared by stepwise dilution of each test solution comprising the components in Tables U1 and U2 with sterilized ion-exchanged solution. The cells were allowed to contact the test solution for 3 minutes at room temperature. A 50 μl of the cell contacted suspension was sampled within 10 seconds, and was seeded on the micro-plate that was used in the R1 test and filled with 0.2 ml of the same culture medium as used in the post-R1 test. The same culture and measurements as used in R1 were conducted thereafter.

[U1-2] Moldicide Test

Cell suspension was obtained by the same method as in the R2 test (cell concentration about $10^5$ cells/ml). A 0.1 ml aliquot of the cell suspension was sampled, and was injected into an aqueous solution (25° C.) prepared by stepwise dilution of the test aqueous solution comprising the components in Table U1 and U2 with sterilized water. After allowing the cells to contact the test aqueous solution for 10 seconds, a 0.1 ml aliquot of this suspension was sampled. Cell growth was observed on the same post-culture PDA medium as used in the R2 test, and was evaluated as in the R2 test.

TABLE U1

| | | | | | | | | Example | | | | | | |
|---|---|---|---|---|---|---|---|---|---|---|---|---|---|---|
| | | | U1 | U2 | U3 | U4 | U5 | U6 | U7 | U8 | U9 | U10 | U11 | U12 |
| Bactericide composition Blended components (weight %) | | | | | | | | | | | | | | |
| (A) | Sodium hypochlorite | | 2.1 | 1.05 | 2.1 | 1.05 | 1.05 | 2.1 | 1.05 | 2.1 | 1.05 | 1.05 | 2.1 | 1.05 |
| | Hypochlorous acid | | | | | | | | | | | | | |
| (B) | Glycerin fatty acid ester[1] | | 1 | 1 | | | | | | | | | | |
| | Polyglycerin fatty acid ester[2] | | | | 1 | 1 | 2 | | | | | | | |
| | Propyleneglycol fatty acid ester[3] | | | | | | | 1 | 1 | | | | | |
| | Sucrose fatty acid ester[4] | | | | | | | | | 1 | 1 | 2 | | |
| | Sorbitan fatty acid ester[5] | | | | | | | | | | | | 1 | 1 |
| | Alkyl polyglycoside[6] | | | | | | | | | | | | | |
| (C) | Fumaric acid | | 1.5 | 1 | | | | | | | | | 2 | 1 |
| | Succinic acid | | | | 2 | 1 | 1 | | | 2 | 1 | 1 | | |
| | Disodium succinic acid | | | | | | | | | | | | | |
| | Citric acid | | | | | | | 2 | 1 | | | | | |
| | Phosphoric acid | | | | | | | | | | | | | |
| Bactericidal test | | | | | | | | | | | | | | |
| Test solution | Available chlorine concentration (ppm) | | 1000 | 1000 | 1000 | 1000 | 1000 | 1000 | 1000 | 1000 | 1000 | 1000 | 1000 | 1000 |
| | pH (20° C.) | | 6.1 | 5.2 | 6.2 | 6.2 | 6.2 | 5.5 | 5.5 | 6.2 | 6.2 | 6.2 | 5.2 | 5.2 |
| Bactericidal activity | Minimum bactericidal concentration (ppm) | Bacillus cereus | 250 | 250 | 62.5 | 62.5 | 62.5 | 250 | 250 | 125 | 125 | 125 | 125 | 125 |
| | | Bacillus subtilis | 125 | 125 | 31.3 | 62.5 | 62.5 | 125 | 125 | 62.5 | 6.2 | 6.2 | 6.2 | 6.2 |
| | | Fungi | 250 | 125 | 62.5 | 62.5 | 31.3 | 250 | 125 | 62.5 | 62.5 | 31.3 | 62.5 | 62.5 |

TABLE U2

| | | | | Example | | | | | | | Comparative example | | | |
|---|---|---|---|---|---|---|---|---|---|---|---|---|---|---|
| | | U13 | U14 | U15 | U16 | U17 | U18 | U19 | U20 | U1 | U2 | U3 | U4 |
| Bactericide composition Blended components (weight %) | | | | | | | | | | | | | | |
| (A) | Sodium hypochlorite | 1.05 | 2.1 | 1.05 | 1.05 | | | 1.05 | 1.05 | 1.05 | | 1.05 | 1.05 |
| | Hypochlorous acid | | | | | 2.1 | 2.1 | | | | | | | |
| (B) | Glycerin fatty acid ester[1] | | | | | | | | | | | | | |
| | Polyglycerin fatty acid ester[2] | | | | | 1 | | 1 | | | 1 | 1 | | |
| | Propyleneglycol fatty acid ester[3] | | | | | | | | | | | | | |
| | Sucrose fatty acid este[4] | | | | | | | | | | | | | |
| | Sorbitan fatty acid ester[5] | 2 | | | | | | | | | | | | |
| | Alkyl polyglycoside[6] | | 1 | 1 | 2 | | 1 | | 1 | | | | | 1 |
| (C) | Fumaric acid | 1 | | | | | | | | | | | | |
| | Succinic acid | | 2 | 1 | 1 | | | | | 1 | 1 | | | 25 |
| | Disodium Succininc acid | | | | | pH adjusta- ble amount | pH adjusta- ble amount | | | | | | | |
| | Citric acid | | | | | | | | | | | | | |
| | Phosphoric acid | | | | | | | 1 | 1 | | | | | |

TABLE U2-continued

|  |  | Example ||||||||| Comparative example ||||
| --- | --- | --- | --- | --- | --- | --- | --- | --- | --- | --- | --- | --- | --- |
|  |  | U13 | U14 | U15 | U16 | U17 | U18 | U19 | U20 | U1 | U2 | U3 | U4 |
| Bactericidal test |  |  |  |  |  |  |  |  |  |  |  |  |  |
| Test solution | Available chlorine concentration (ppm) | 1000 | 1000 | 1000 | 1000 | 125 | 125 | 1000 | 1000 | 1000 | 1000 | 1000 | 1000 |
|  | pH (20° C.) | 5.2 | 6.2 | 6.2 | 6.2 | 6.0 | 6.0 | 6.0 | 6.0 | 6.2 | 3.5 | 9.0 | 8.5 |
| Bactericidal activity |  |  |  |  |  |  |  |  |  |  |  |  |  |
| Minimum bactericidal concentration (ppm) | *Bacillus cereus* | 125 | 31.3 | 62.5 | 62.5 | 62.5 | 31.3 | 125 | 62.5 | 1000 | over 1000 | over 1000 | over 1000 |
|  | *Bacillus subtilis* | 625 | 31.3 | 31.3 | 31.3 | 31.3 | 31.3 | 62.5 | 62.5 | 500 | over 1000 | over 1000 | over 1000 |
|  | Fungi | 31.3 | 31.3 | 31.3 | 31.3 | 62.5 | 31.3 | 125 | 62.5 | over 1000 | over 1000 | over 1000 | over 1000 |

[1] Excel VS-95 (made by Kao Corp.)
[2] MCA-750 (made by Sakamoto Pharmaceutical Industry Co.)
[3] Homotex PS-200 (made by Kao Corp.)
[4] LWA1570 (made by Mitsubishi Foods Co.)
[5] Emasol O-10 (made by Kao Corp.)
[6] Mydol 12 (made by Kao Corp.)

The phrase "pH adjusting amount" of the component (C) in Examples U17 and U18 means an amount by which the pH value of the test aqueous solution becomes that in Table U1.

What is claimed is:

1. A liquid bactericide composition comprising:
   hypochlorous acid or an alkali metal salt thereof (A),
   a surfactant (B), and
   a pH adjusting agent (C),
   wherein said composition is an aqueous solution having a pH value (25° C.) of 5 to 7 and
   wherein the weight ratio of (A)/(B) in the aqueous solution is in the range of 2/1 to 1/2, and
   the weight ration of (C)/(A) in the aqueous solution is in the range of 2/1 to 1/5, and the available chlorine concentration of (A) in the aqueous solution if from 25 to 500 ppm.

2. The bactericide composition according to claim 1, wherein the weight ratio (C)/(A) between the pH adjusting agent (C) and hypochlorous acid and/or a salt thereof (A) is 1/1 to 1/5.

3. The bactericide composition according to claim 1, wherein the surfactant (B) is at least one selected from the group consisting of amphoteric surfactants, cationic surfactants and nonionic surfactants.

4. The bactericide composition according to claim 1, wherein the surfactant (B) is an amine oxide.

5. The bactericide composition according to claim 1, wherein the surfactant (B) is a polyhydric alcohol derivative surfactant.

6. The bactericide composition according to claim 1, wherein the pH adjusting agent (C) is an organic acid or a salt thereof.

7. The bactericide composition according to claim 6, wherein the organic salt or a salt thereof is a saturated dibasic acid or a salt thereof.

8. A bactericide comprising the liquid bactericide composition of claim 1, wherein components (A), (B) and (C) are individual components and then mixed together to obtain said liquid bactericide therefore composition.

9. A bactericide comprising liquid bactericide composition of claim 1, wherein component (A) is an individual component that is mixed with components (B) and (C) to obtain said liquid bactericide therefore composition.

10. A bactericide comprising liquid bactericide composition of claim 1, wherein component (C) is an individual component that is mixed with components (A) and (B) to obtain said liquid bactericide therefore composition.

11. The bactericide according to any one of claims 8 to 10, wherein the pH adjusting agent (C) is an organic acid or a salt thereof.

12. The bactericide according to claim 11, wherein the organic acid or a salt thereof is a dibasic organic acid or a salt thereof.

13. The bactericide according to claim 8, wherein the surfactant (B) is at least one selected from the group consisting of amphoteric surfactants, cationic surfactants and nonionic surfactants.

14. The bactericide according to claim 8, wherein the surfactant (B) is an amine oxide.

15. The bactericide according to claim 8, wherein the surfactant is a polyhydric alcohol derivative surfactant.

16. The bactericide composition according to claim 1, wherein said alkali metal salt of hypochlorous acid is selected from the group consisting of sodium hypochlorite, potassium hypochlorite and lithium hypochlorite.

* * * * *

UNITED STATES PATENT AND TRADEMARK OFFICE
CERTIFICATE OF CORRECTION

PATENT NO. : 6,793,846 B2 Page 1 of 1
APPLICATION NO. : 10/149147
DATED : September 21, 2004
INVENTOR(S) : Kiyoaki Yoshikawa et al.

It is certified that error appears in the above-identified patent and that said Letters Patent is hereby corrected as shown below:

In Claim 1, column 23, line 40:

"if" should read as --is--.

Signed and Sealed this

Thirty-first Day of October, 2006

JON W. DUDAS
*Director of the United States Patent and Trademark Office*